(12) United States Patent
Oostman, Jr.

(10) Patent No.: US 9,974,565 B2
(45) Date of Patent: May 22, 2018

(54) INSTRUMENTS, SYSTEMS AND METHODS FOR IMPROVING HAIR TRANSPLANTATION

(71) Applicant: Restoration Robotics, Inc., San Jose, CA (US)

(72) Inventor: Clifford A. Oostman, Jr., Hansville, WA (US)

(73) Assignee: RESTORATION ROBOTICS, INC., San Jose, CA (US)

( * ) Notice: Subject to any disclaimer, the term of this patent is extended or adjusted under 35 U.S.C. 154(b) by 320 days.

(21) Appl. No.: 14/718,441

(22) Filed: May 21, 2015

(65) Prior Publication Data

US 2016/0338732 A1 Nov. 24, 2016

(51) Int. Cl.
| | |
|---|---|
| *A61B 17/34* | (2006.01) |
| *A61B 34/30* | (2016.01) |
| *A61B 17/00* | (2006.01) |
| *A61B 90/00* | (2016.01) |

(52) U.S. Cl.
CPC .......... *A61B 17/3468* (2013.01); *A61B 34/30* (2016.02); *A61B 90/06* (2016.02); *A61B 2017/00752* (2013.01); *A61B 2090/061* (2016.02)

(58) Field of Classification Search
CPC .......... A61B 34/30; A61B 2017/00752; A61B 17/3468
See application file for complete search history.

(56) References Cited

U.S. PATENT DOCUMENTS

| | | | |
|---|---|---|---|
| 4,026,171 A | 5/1977 | Kubacki et al. |
| 4,154,239 A | 5/1979 | Turley |
| 4,400,170 A | 8/1983 | McNaughton et al. |
| 4,451,254 A | 5/1984 | Dinius et al. |
| 4,474,572 A | 10/1984 | McNaughton et al. |
| 5,417,683 A | 5/1995 | Shiao |
| 5,439,475 A | 8/1995 | Bennett |
| 5,584,851 A | 12/1996 | Banuchi |
| 5,611,811 A | 3/1997 | Goldberg |
| 5,643,308 A | 7/1997 | Markman |
| 5,782,843 A | 7/1998 | Aasberg |
| 5,782,851 A | 7/1998 | Rassman |

(Continued)

FOREIGN PATENT DOCUMENTS

| | | |
|---|---|---|
| WO | WO 1992/000706 | 1/1992 |
| WO | WO 1995/028896 | 11/1995 |

(Continued)

OTHER PUBLICATIONS

PCT International Search Report and the Written Opinion dated Aug. 11, 2016, in connection with commonly assigned International Application No. PCT/US2016/031878, (18 pages).

(Continued)

*Primary Examiner* — Anh Dang

(57) ABSTRACT

Instruments, systems and methods are provided for efficient loading, indexing and replacement of cartridges for storing, for example, hair grafts. In addition, an improved urging mechanism for expelling hair grafts from a receptacle of a storage cartridge is provided, as well as a method of its operation. Furthermore, cartridges with a plurality of receptacles comprising slots for loading hair grafts are disclosed.

20 Claims, 9 Drawing Sheets

(56) References Cited

U.S. PATENT DOCUMENTS

| | | |
|---|---|---|
| 5,792,169 A | 8/1998 | Markman |
| 5,817,120 A | 10/1998 | Rassman |
| 5,868,758 A | 2/1999 | Markman |
| 5,873,888 A | 2/1999 | Costanzo |
| 5,951,572 A | 9/1999 | Markman |
| 5,989,279 A | 11/1999 | Rassman |
| 6,027,512 A | 2/2000 | Bridges |
| 6,056,736 A | 5/2000 | Markman |
| 6,110,189 A | 8/2000 | Markman |
| 6,585,746 B2 | 7/2003 | Gildenberg |
| 6,973,931 B1 | 12/2005 | King |
| 7,144,406 B2 | 12/2006 | Pak et al. |
| 7,481,820 B1 | 1/2009 | Keene |
| 8,211,134 B2 | 7/2012 | Oostman |
| 8,510,929 B2 | 8/2013 | McMurtry et al. |
| 2003/0040766 A1 | 2/2003 | Werner |
| 2003/0087454 A1 | 5/2003 | Schultz et al. |
| 2004/0162458 A1* | 8/2004 | Green ............... A61M 37/0069 600/7 |
| 2006/0195047 A1 | 8/2006 | Freeman et al. |
| 2007/0078466 A1 | 4/2007 | Bodduluri et al. |
| 2007/0106306 A1 | 5/2007 | Bodduluri et al. |
| 2009/0087830 A1* | 4/2009 | Oostman, Jr. .......... A61B 17/00 435/4 |
| 2010/0106136 A1* | 4/2010 | Simonton ......... A61M 37/0069 604/511 |
| 2015/0133962 A1 | 5/2015 | Oostman |

FOREIGN PATENT DOCUMENTS

| | | |
|---|---|---|
| WO | WO 1998/047434 | 10/1998 |
| WO | WO 2000/025683 | 5/2000 |
| WO | WO 2001/064111 | 9/2001 |
| WO | WO 2001/065996 | 9/2001 |
| WO | WO 2005/009491 | 2/2005 |
| WO | WO 2007/021904 | 2/2007 |
| WO | WO 2007/041267 | 4/2007 |
| WO | WO 2008/066991 | 6/2008 |
| WO | WO 2009/045255 | 4/2009 |

OTHER PUBLICATIONS

Bernstein, et al., "The Logic of Follicular Unit Transplantation", Dermatologic Clinics—vol. 17—No. 2—Apr. 1999, Apr. 1999, pp. (277-296).

Lee, et al., "New Instrument for Hair Transplant: Multichannel Hair Transplanter", Dermatol Surg 2005, 31:379, 2005, 1 page.

Rassman, et al., "Rapid Fire Hair Implanter Carousel", From New Hair Institute—Internet. (Dermatologic Surgery, vol. 24, 1998—pp. 623-627), Feb. 16, 2006, 7 pages.

* cited by examiner

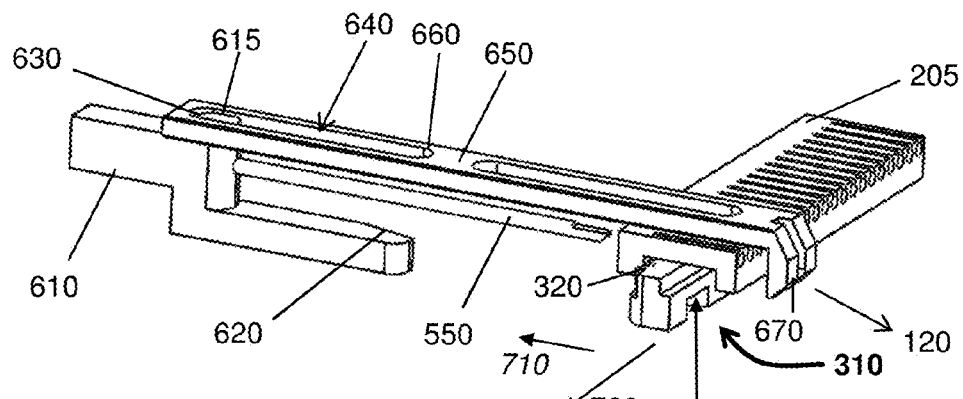
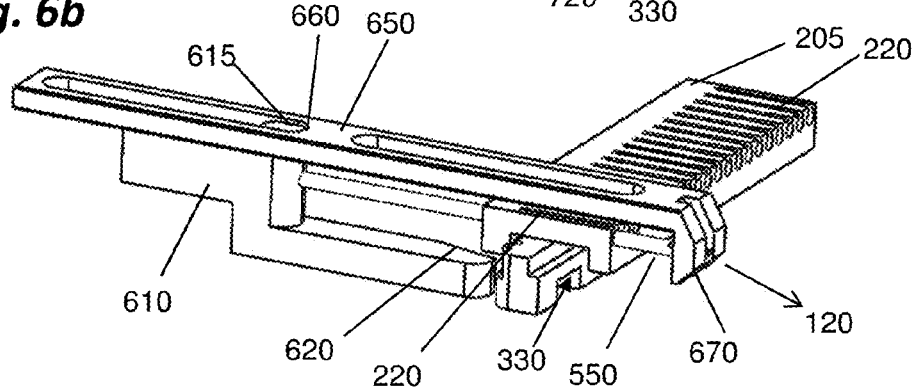
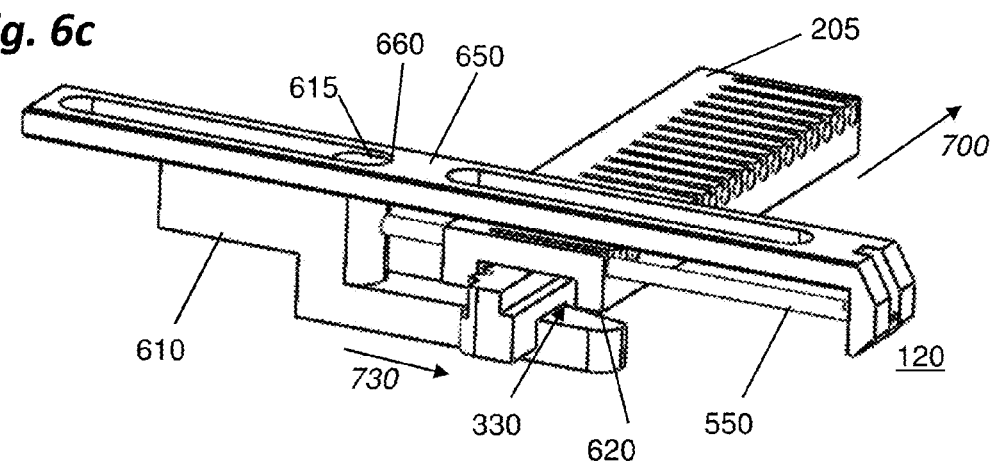

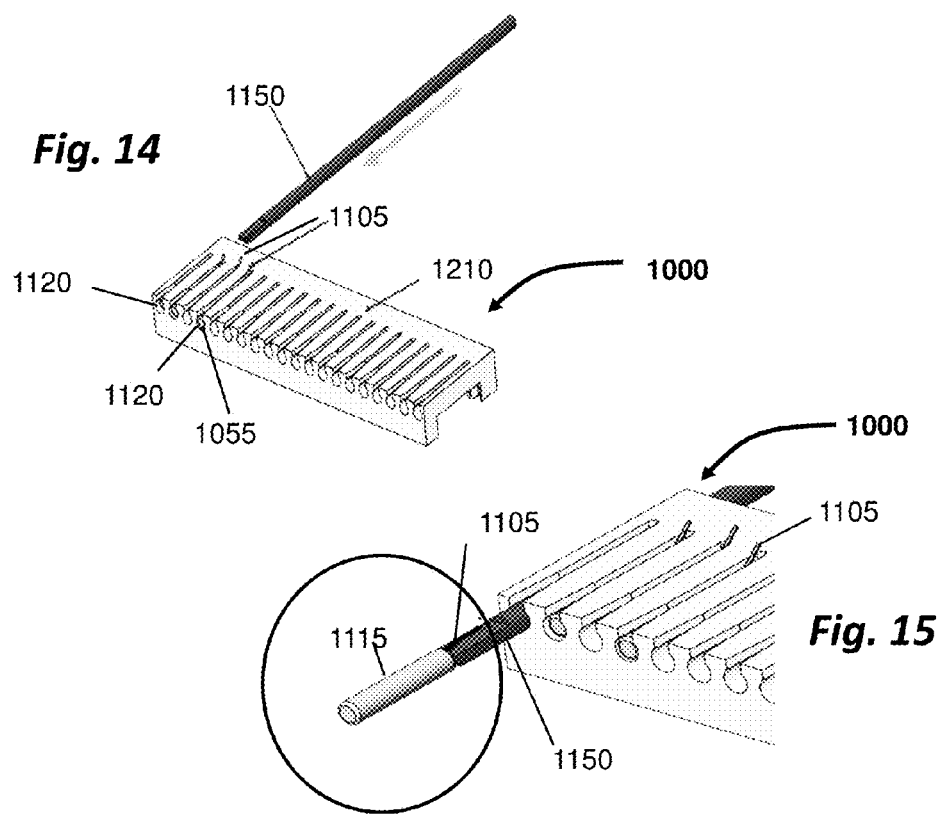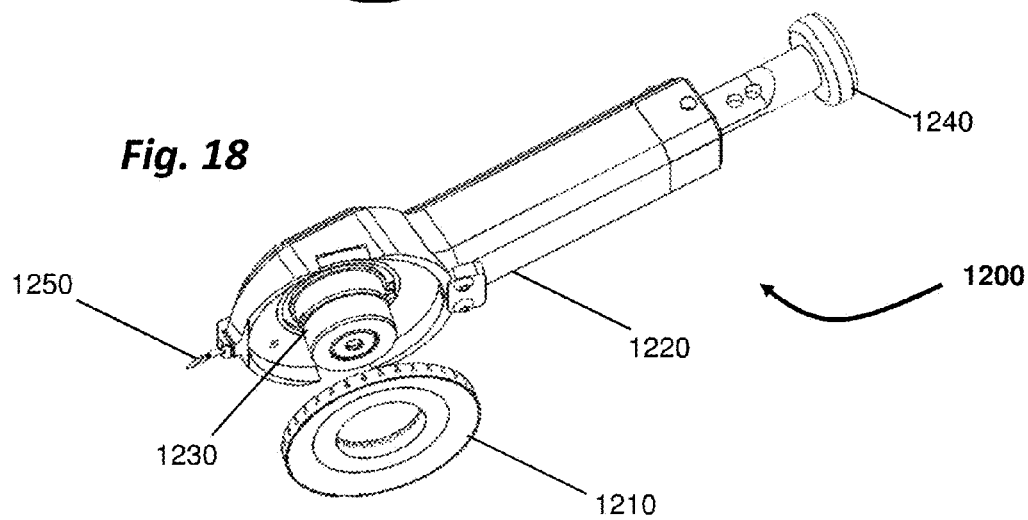

INSTRUMENTS, SYSTEMS AND METHODS FOR IMPROVING HAIR TRANSPLANTATION

TECHNICAL FIELD

The present disclosure relates generally to instruments, systems and methods, such as hair transplantation instruments, systems and methods of their use. In particular, this application relates to automated or semi-automated instruments, systems and methods for implanting hair follicular units or hair grafts, in a body surface, for example, a scalp.

BACKGROUND

With the advancement of technology, various medical and cosmetic procedures may now be performed using various degrees of automation, and often at high speed. Some of these procedures are performed using hand-held tools, in other instances utilizing automated system that may include robotic arms, for example. These procedures include but are not limited to, for example, hair transplantation procedures (hair harvesting and/or hair implantation), dermal implantation, skin grafting and tattooing.

During such manual, semi-automatic, or robotically-assisted procedures, often there is a need to collect and store biological units, for example, for future examination, or processing, implantation or reuse. Generally the medium to be implanted, whether it is a cosmetic jewel or a biological unit, such as follicular unit, is taken from some storage device prior to their implantation. Often these storage devices consist of a container for bulk hair grafts, from which a technician plucks individual grafts for implant. While various storage devices or cartridges were proposed in the past, there is a need for further improvements in such storage device which could be used in manual, partially or fully automated, or robotically-assisted systems and procedures, especially when large quantities of biological units or other items must be stored and processed.

SUMMARY

According to one aspect of the disclosure, a hair transplantation apparatus is provided. The apparatus comprises a first cartridge having at least one first indexing feature and comprising a first plurality of receptacles with a predetermined spacing therebetween, each receptacle sized and configured to retain a follicular unit; a second cartridge having at least one second indexing feature and comprising a second plurality of receptacles with the predetermined spacing therebetween, each receptacle sized and configured to retain a follicular unit; a housing configured to accommodate one or more cartridges; an urging mechanism operative when substantially aligned with one of the first plurality of receptacles of the first cartridge or one of the second plurality of receptacles of the second cartridge to load the follicular unit into the receptacle or expel the follicular unit from the receptacle; and an indexing mechanism comprising at least one corresponding indexing feature configured to engage with the at least one first indexing feature of the first cartridge and/or the at least one second indexing feature of the second cartridge and to move the first and/or the second cartridge to align a receptacle of the first or the second plurality of receptacles with the urging mechanism. The apparatus is configured to operatively couple the first cartridge to a second cartridge such that a distance between a last receptacle of the first cartridge and a first receptacle of the second cartridge equals the predetermined spacing and wherein the urging mechanism is configured to move into alignment with the first receptacle of the second cartridge without disconnecting the first cartridge from the apparatus.

In some embodiments the apparatus may comprise an indicator configured to inform when the last receptacle of the first cartridge has been or is about to be emptied or filled. In other embodiments at least one of the first cartridge or the second cartridge may comprise fiducials configured to indicate: 1) a type of follicular unit contained therein, and/or 2) whether an end of the cartridge has been reached. The apparatus may be configured to automatically disconnect the first cartridge substantially at the same time or after at least one follicular unit is expelled from or loaded into the first receptacle of the second cartridge.

In certain embodiments the urging mechanism may comprise a pressure differential. In other embodiments the urging mechanisms may comprise an obturator sized and configured to pass through a selected receptacle of the first or second cartridge. Retraction of the obturator from the selected receptacle may cause the first and/or second cartridge to index. The obturator may comprise a recess configured to accommodate at least a portion of a hair shaft of the follicular unit.

According to another aspect of the disclosure, an apparatus is provided which may be removably received in a robotic hair transplantation system comprising a robotic arm, a control mechanism, and an implanting tool having a lumen therethrough and being connected to and manipulated by the robotic arm. The control mechanism may be adapted to automatically align the selected cartridge receptacle with the lumen of the implanting tool and urge the follicular unit from the selected receptacle through the lumen of the implanting tool into a body surface. In other embodiments, the apparatus may further comprise a follicular unit removal tool having a lumen therethrough, the removal tool is connected to and manipulated by the robotic arm to position the removal tool over a follicular unit located on a body surface. The control mechanism may be adapted to align the lumen of the removal tool with a selected cartridge receptacle and urge the FU through the removal tool into the selected cartridge receptacle.

According to a further aspect of the disclosure, a method of continuous feeding of cartridges during hair transplantation procedure is provided. In some implementations, the method comprising the steps of: loading a first cartridge comprising a first plurality of receptacles into a hair transplantation system, each of the first plurality of receptacles sized and configured to retain a follicular unit and separated from adjacent receptacles by a predetermined distance; aligning an urging mechanism with a receptacle of the first plurality of receptacles of the first cartridge; coupling a second cartridge comprising a second plurality of receptacles to the hair transplantation system, each of the second plurality of receptacles sized and configured to retain a follicular unit and separated from adjacent receptacles by the predetermined distance; and aligning the urging mechanism with a first receptacle of the second cartridge without first removing or disconnecting the first cartridge from the hair transplantation system. In some embodiments, the method further comprises activating the urging mechanism to urge a hair graft out of or into the receptacle of the first plurality of receptacles. In some embodiments, the method may comprise manually or automatically disconnecting the first cartridge substantially either at the time or after at least one follicular unit is expelled from or loaded into the first receptacle of the second cartridge.

In a still further aspect of the disclosure, a method of continuous feeding of cartridges for use in at least partially automated procedure is provided, the method comprising the steps of: loading a first cartridge comprising a first plurality of receptacles into a system, each of the first plurality of receptacles is sized and configured to retain a biological unit and separated from adjacent receptacles by a predetermined distance; aligning an urging mechanism with a receptacle of the first plurality of receptacles of the first cartridge; coupling a second cartridge comprising a second plurality of receptacles to the system, each of the second plurality of receptacles is sized and configured to retain a biological unit and separated from adjacent receptacles by the predetermined distance; and aligning the urging mechanism with a first receptacle of the second cartridge without first removing or disconnecting the first cartridge from the system. In some embodiments, the method further comprises activating the urging mechanism to urge a biological unit out of or into the receptacle of the first plurality of receptacles.

According to yet further aspect of the disclosure, an urging mechanism for expelling follicular units out of a receptacle of a storage cartridge is provided, the urging mechanism comprising an elongated body having a distal end with a distal tip. In some embodiments, the urging mechanism may comprise a recess disposed on a first side along the distal end of the elongated body, the recess disposed at the distal tip and having a length to accommodate only a tip portion of the follicular unit to be stored in the receptacle of the storage cartridge. The recess may comprise a depth, for example, in a range from about 0.15 mm to 0.25 mm, or in a range of about 10% to about 30% of a cross-sectional dimension of the elongated body of the urging mechanism. When the urging mechanism is aligned with a follicular unit in tandem such that a proximal end of a tissue portion of the follicular unit is adjacent the distal tip of the elongated body of the urging mechanism, the tip portion of the follicular unit is fully accommodated by and extends along the length of the recess of the elongated body.

In other embodiments, the urging mechanism may comprise a cut-out portion at the distal end of the elongated body, the cut-out portion may be disposed at the distal tip and at an angle to the distal tip. The angle of the cut-out may be, for example, between 40 degrees and 50 degrees. The cut-out portion may extend, for example, from about 25 percent to about 60 percent of a cross-sectional dimension of the elongated body of the urging mechanism. The angle of the cut-out portion may be based on a desired angle or a range of angles at which an urging mechanism is aligned with a body surface during operation such that a surface of the cut-out portion substantially flush with a surface of a body surface. In further embodiments the urging mechanism may comprise both a recess and a cut-out portion, for example, on the opposite sides of the distal end of the urging mechanism.

According to yet another aspect of the present disclosure, a storage cartridge of the improved design is provided. The cartridge comprises a plurality of receptacles for holding, for example, follicular units or hair grafts. The cartridge may comprise a top surface, a bottom surface and a first (or front) face and a second (or rear) face. The receptacles each pass through a body of the cartridge from a first face to a second face and comprise a slot extending along at least a portion of the length of the receptacle and opening on the top surface of the cartridge.

Instruments, systems and methods of the present disclosure may be implemented for use with manual, partially automated and fully automated, including robotic, systems and procedures, for example, for implantation of biological units, including follicular units. Other and further objects and advantages of the disclosure will become apparent from the following detailed description when read in view of the accompanying figures.

BRIEF DESCRIPTION OF THE DRAWINGS

It should be noted that the drawings are not to scale and are intended only as an aid in conjunction with the explanations in the following detailed description. In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to be limiting. Features and advantages of the embodiments described herein will become appreciated as the same become better understood with reference to the specification, claims, and appended drawings wherein:

FIGS. 6a-6c illustrate an example of an indexing mechanism according to the present disclosure;

FIG. 14 shows a follicular unit being expelled from the linear cartridge, such as the cartridge of the example of FIG. 11;

FIG. 15 shows a schematic representation of an example of an obturator according to the present disclosure and its use with the cartridge of the present disclosure;

FIG. 18 is an example of a hand-held apparatus for hair transplantation that can be used with devices, systems and methodology of the present disclosure.

DETAILED DESCRIPTION OF SPECIFIC EMBODIMENTS

Figure 1:
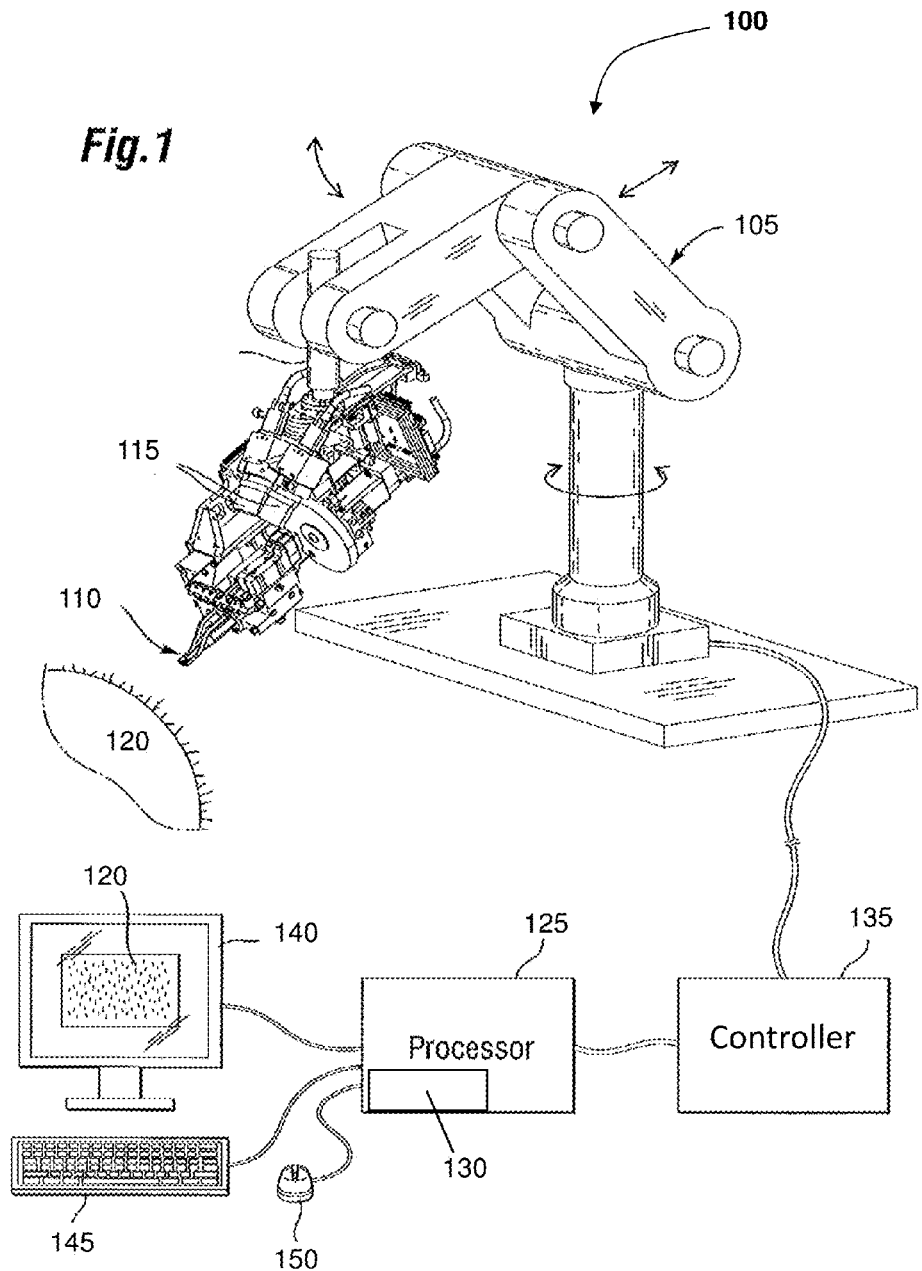
FIG. 1 is a schematic perspective view of an example of a robotic system that could be utilized with the devices and method of the present disclosure.

In the following Detailed Description, reference is made to the accompanying drawings, in which are shown by way of illustration specific embodiments in which the invention may be practiced. In this regard, directional terms such as "top," "bottom,", "upper", "lower", "front," "back," "distal," "proximal," etc., are used with reference to the orientation of the Figure(s) being described. Because components or embodiments of the present disclosure can be positioned in a number of different orientations, the directional terminology is used for purposes of illustration and is in no way limiting. It is to be understood that other embodiments may be utilized and structural or logical changes may be made without departing from the scope of the present disclosure. The following Detailed Description, therefore, is not to be taken in a limiting sense, and the scope of the present disclosure is defined by the appended claims.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts requiring manual input.

The term "tool," as used herein refers to any number of tools or end effectors that are capable of performing an action, procedure or operation in various cosmetic, medical procedures or applications. For example, the tool may be a needle or cannula adapted for use in various dermatological applications, tissue grafting, injection of fat cells, for example, into a subcutaneous fat layer for facial or body "lipo-contouring", collagen implantation, injection of hyaluronic acid products and/or muscle inhibitors (e.g., Botox®), procedures for facial or body rejuvenation or reconstruction, for example, involving making a number of injections of minute amounts of substances into targeted intradermal and subcutaneous tissues, or the administration of medication. A "tool" or "implanting tool" as used in reference to a hair transplantation procedure refers to any number of tools or end effectors that are capable of implanting/inserting follicular units ("FUs") to a body surface. Such tools may have many different forms and configurations. In some embodiments, the tool comprises a hollow tubular shaft. The distal end of the tools (for example, punches, coring devices, cutting and/or trimming devices, needles), are typically sharpened, to cut the tissue. Implanting tools may also be sharpened so as to perform puncture and delivery of the FU in one operation. However, the puncture may be formed by another tool, with the implanting tool being relatively blunt and used just for delivery of the follicular unit.

The terms "operatively connected," "coupled," "mounted" or "attached" as used herein, means directly or indirectly coupled, mounted or attached through one or more intervening components. Embodiments of the methods of the present disclosure may be implemented using computer software, firmware or hardware. Various programming languages and operating systems may be used to implement the present disclosure.

Continuous Feed of Objects into a Tool and Use of Multiple Storage Devices

According to one aspect of the present disclosure, the systems and methods are provided that allow for a continuous feed of objects into a tool, which, for example, can then be implanted into a body surface. Although the various examples and embodiments described herein will use implantation of the follicular units (naturally occurring aggregates of 1 to 4 hair follicles) or hair grafts for purposes of describing various aspects of the disclosure, it should be apparent that the general understanding of the various concepts discussed can be applied more broadly to other appropriate applications. Various applications and procedures where it is beneficial to store objects for use in the procedure, where the procedure involves a large number of objects that could be stored in multiple cartridges, or where it is important to avoid damaging the objects to be stored, may benefit from the system, devices and methods of the present disclosure. It should be understood that the devices, systems and methods described herein may be utilized, for example, in medication delivery, various dermatological procedures or treatment of various dermatological conditions. Similarly, the present disclosure may be applied, for example, to other objects which may be implanted into a body surface, for example, fat cells, medication, or dermal implants such as body jewelry, which may take the form or subdermal, transdermal or microdermal implants, tattooing, or various biological units, including skin, tissue, or hair. The present disclosure is particularly beneficial in semi-automated, automated, or robotic procedures, such as robotic hair transplantation procedures.

For purposes of the description, in reference to hair transplantation, hand held instruments exist which enable a user to manually create an incision in a body surface and simultaneously or subsequently move a follicular unit which was previously loaded into the hand held instrument into the body surface. According to some known devices, the follicular units are loaded into a cartridge associated with the hand held instrument, for example, as described in the U.S. Pat. No. 5,817,120 to Rassman. However, such devices have limited capabilities. For example, the device of the U.S. Pat. No. 5,817,120 has a single cartridge that contains a limited number of hair grafts. Once all hair grafts from such a cartridge are implanted, the procedure has to be interrupted or stopped, in order to reload new grafts into the cartridge, or alternatively, the empty cartridge must be removed and a new cartridge installed in order to continue the procedure. Commonly assigned U.S. Pat. No. 8,211,134 describes systems and methods for harvesting, storing and implanting biological units, including examples of cartridges, systems and a shuttle subsystem that may form part of a manual, partially automated or robotic hair transplantation apparatus.

One issue that is not adequately addressed by the known cartridges, including those for use in manual or automated procedures, is the need to efficiently replace or reload an empty cartridge (e.g., once all of the follicular units within the cartridge have been unloaded from the cartridge and implanted into the patient) with a new one. Generally, stopping or terminating the procedure is required so that the user can either throw away a disposable hair implantation instrument and obtain another one, or remove the empty cartridge from the automated system so that another cartridge can be inserted into such automated system. No matter what the reason, the procedure typically needs to be terminated, and delays in being able to seamlessly continue the procedure cause valuable time to be lost. With respect to a robotic procedure, removal and subsequent replacement of a cartridge may additionally require that the robotic apparatus be re-calibrated, causing to further extend the hair transplantation procedure. To summarize, the existing devices do not allow for convenient and efficient replacement and loading of multiple cartridges, especially with minimal interruption of the procedure. The present disclosure provides devices, systems and methods for addressing this issue.

According to one aspect of the present disclosure, a continuous feed of follicular units is maintained to a follicular unit implantation tool, whether the tool be attached to a manual or an at least partially automated procedure, such that the need for the user to stop the procedure in order to insert another loaded cartridge into his manual or at least partially automated apparatus is minimized.

FIG. 1 is a schematic perspective view of an example of a robotic system 100 that may be used, for example, for harvesting and/or implanting follicular units into a body surface, such as the scalp. The system 100 includes a robotic arm 105 to which is coupled a tool 110, for example a harvesting or implanting tool. Various motors and other movement devices may be incorporated to enable fine movements of an operating tip of the tool 110 in multiple directions. The robotic system 100 further includes at least one or more (and preferably two for stereo vision) image acquisition device 115 which may be mounted in a fixed position, or coupled (directly or indirectly) to a robotic arm 105 or other controllable motion device. The image acquisition device 115 may comprise a device that takes still images, it can also comprise a device capable of real time imaging (e.g., webcam capable of continuously streaming real time information), and/or it could also have a video recording capability (such as a camcorder). The image acquisition device may be coupled to one or more processor or a processing system 125, which in the example of FIG. 1 incorporates an image processor 130, to control the imaging operation and process image data. The operating tip of the tool 110 is shown positioned over a body surface 120, in this case a part of the patient scalp having hair follicles thereon.

Typically, the processor 125 operates as a data processing device, and may execute a program that may be configured to include predetermined operations and may be incorporated into a computer. Alternatively, the program may include a plurality of modules that perform such sub-operations of an operation, or may be part of a single module of a larger program providing the operation. The modular construction facilitates adding, deleting, updating and/or amending the modules therein and/or features within the modules. The processor may access the memory in which may be stored at least one sequence of code instructions comprising the program for performing predetermined operations. The memory and the program may be located within the computer or may be located external thereto. The processor 125 may include a central processing unit or parallel processor, and input/output interface, a memory with a program, wherein all the components may be connected by a bus. These components are generally known in the art and, therefore, they do not need to be described in detail here.

The processor 125 may comprise an image processor 130 for processing images obtained from the image acquisition device 115. The image processor 130 may be a separate device or it may be incorporated as a part of the processor 125. By way of example, and not limitation, a suitable image processor 130 may be a digital processing system which includes one or more processors or other type of device. For example, a processor and/or an image processor may be a controller or any type of personal computer ("PC"). Alternatively, the processor may comprise an Application Specific Integrated Circuit (ASIC) or Field Programmable Gate Array (FPGA). The processor/image processor may also include memory, storage devices, and other components generally known in the art and, therefore, they do not need to be described in detail here.

The processor 125 may also instruct the various movement devices of the robotic arm 105, including the tool 110, and act, for example, through a controller 135 as schematically shown in FIG. 1. The controller 135 may be operatively coupled to the robotic arm and configured to control the motion of the robotic arm, including the motion based on the images or data acquired by the image acquisition device. Alternatively, controller 135 may be incorporated as a part of the processor 125, so that all processing and controls of all movements of all the tools, the robotic arm and any other moveable parts of the assembly, including those based on the images or data acquired by the image acquisition device, are concentrated in one place. The system 100 may further comprise other tools, devices and components useful in harvesting, and/or implantation of the hair follicles, or in hair transplantation planning.

The system further comprises an interface adapted to receive an image data, various parts of the system allowing an operator to monitor conditions and provide instructions, as needed. A user interface may comprise elements such as a display device 140, and user input devices such as a keyboard 145 and mouse 150. The interface may also include hardware ports, cables, leads, and other data transmission means, or it may comprise a computer program. The processor 125 may interact with the imaging device 115 via the interface. It will be apparent that the user input device may optionally comprise a track pad, track ball, stylus, pen or line tool in combination with a touch-enabled device, tablet or other such similar device on which one may use one's fingers or gestures, to input commands. A magnified image of the body surface 120 can be seen on the display device, screen or monitor 140. In addition, the system 100 may comprise other tools, devices and components useful in harvesting, and/or implantation of the hair follicles, or in hair treatment planning.

Figure 2:
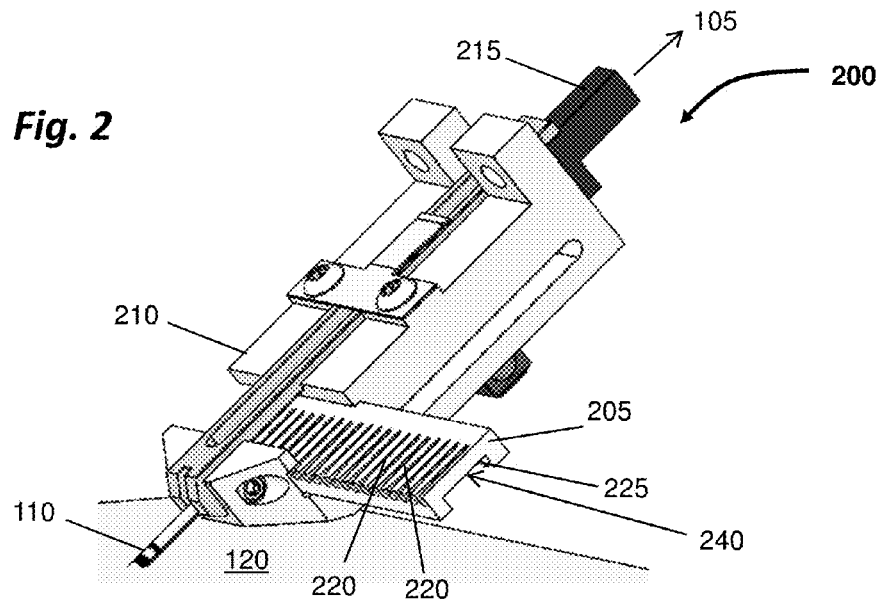
FIG. 2 is a schematic perspective view of an example a follicular implantation system with one follicular unit cartridge.

FIG. 2 illustrates various components of a follicular unit implantation system 200 which may be coupled to the end of robotic arm 105 of a robotic system 100, the follicular unit implantation system 200 incorporating a follicular unit cartridge 205. The follicular unit implantation system 200 comprises a tool assembly housing 210 which may be configured such that it can be attached to the end of a robotic arm 105 of a robotic system, such as those shown in FIG. 1, or it may be operatively connected or form a part of a hand-held device, such as that shown in FIG. 18. To optimize the utilization of the robotic system for the purposes of hair transplantation, in some embodiments the housing 210 is coupled to the end of the robotic arm 105 by a rotation mechanism 215 which is configured such that the housing 210 is allowed to rotate about an axis substantially parallel to the length of the tool 110. In this manner, under appropriate instructions the rotation mechanism 215 is able to rotate the housing 210, and consequently the tool 110 attached thereto.

The cartridge 205 comprises a plurality of receptacles, each receptacle 220 sized and configured to retain a follicular unit (or other appropriate object, biological or otherwise). Moreover, such cartridge 205 preferably permits storage of the follicular units under an at least partially controlled environment, for example, keeping them sterile, moist, and/or at a desired cool temperature until they are required to be implanted into the body surface 120. Desirably, an amount of saline or other known preserving solution is placed in each receptacle of the cartridge so that hair follicles or other biological objects remain hydrated or maintain a cool temperature during the storage. Alternatively, or additionally, the cartridge 205 may be placed in a vessel such as a petri dish containing saline or other such preservation solution to maintain the health of the follicular unit until such time that the cartridge is required for use with the implantation system. The shape or configuration of the cartridge 205 may take various forms, and may depend upon the application. FIG. 2 illustrates a linear cartridge. Preferably the cartridge 205 can be sterilized so it can be reused. Alternatively, the cartridge may be manufactured to be disposable, or such that its reuse is prevented, and thus it is disposable.

A typical hair transplantation procedure on a balding male requires the implantation of between 1,500 and 3,000 hair grafts. The utilization of a single cartridge 205 configured to accommodate such a large number of follicular units (or hair grafts) would not be practical due to numerous reasons. Apart from the fact that the cartridge would be extremely long and difficult to load, its use would create practical problems and limitations. First, since the cartridge 205 is utilized adjacent the patient's head or body surface 120, the portion of the cartridge 205 from which the follicular units have been expelled cannot be too long in length as it will collide with the patient's head or body surface 120, particularly if the rotation mechanism 215 is rotated such that an end of the cartridge points towards the patient's head. Second, a typical hair transplantation procedure requires the implantation of certain types of hair grafts, that is natural aggregates of 1-3 (and less commonly, 4-5) closely spaced hair follicles, follicular units, into different areas of the patient's head. These follicular units may be classified, or "typed", based on the number of hair in the unit and identified in shorthand as an "F1" for a single follicular unit, an "F2" for a two hair follicular unit and so on for follicular units with 3-5 hairs. It is preferable to transplant certain types of follicular units into specific regions of the scalp. For example, single hair follicular units (F1s) are commonly implanted along the hairline that frames the face. Follicular units with more than one hair (F2s, F3s, etc.) are commonly implanted in the mid-scalp and crown. This arrangement of follicular unit distribution is thought to produce a more natural appearing aesthetic result, along with a variation in density of hair, the direction or orientation of hair, the particular mix of types of follicular units, and/or the appearance of randomness, which attribute to a more natural looking appearance of the transplanted hair. Therefore the utilization a single long cartridge loaded with random types of follicular units would be less efficient and may limit the speed at which a hair transplantation procedure could be performed. The user or the system would need to identify the type of the follicular unit in the cartridge before implanting it and then move randomly back and forth to various regions of the patient's head to implant such follicular units.

The ability to continue a treatment plan or procedure without the need to stop to either reload a cartridge with implant units, to replace a filled cartridge with an empty one, or to replace an empty cartridge with a filled one provides numerous advantages. From the physician's perspective, valuable time could be saved, requiring less down-time and shorter procedures (which could likely to improve the quality as well). Moreover, it may allow physicians to treat more patients during the day, and therefore increase his/her earning potential. Time could be saved at one or more stages of a hair transplantation procedure, including for example by providing for a continuous supply of empty cartridges into which follicular units harvested from the body surface of a patient can be stored, and/or providing a continuous supply of cartridges filled with follicular units for implanting into a patient's body surface. From the patient's perspective, fewer interruptions would potentially mean the patient would be treated for a shorter period of time, reducing the duration of any discomfort associated with such a procedure. According to one aspect of the current disclosure, efficiency of the procedure and associated devices/instruments is substantially improved by allowing multiple cartridges to be used in an efficient way, for example substantially continuously, without requiring the need to interrupt the procedure. A length of a cartridge sufficient to accommodate a number, for example, in the range of twenty to thirty follicular units allows for these practicalities to be addressed, while still providing a large enough number to optimize the procedure time. Though shown to accommodate twenty (20) follicular units, the length of the cartridge 205 will ultimately depend upon constraints dictated by the procedure which is being performed, the object which is to be stored with the cartridge, and the apparatus to which it is to be coupled. Another advantage of utilizing more than one cartridge is that each cartridge may be loaded with follicular units of a particular type, for example, all F2 in one cartridge, or all F1 placed to the neighboring receptacles in one half of the cartridge while the other half of the cartridge has F2 grouped together in the neighboring receptacles.

To assist in identification of the types (classifications) of follicular units each cartridge contains, the cartridge 205 may be configured or marked in such a way that the user, an imaging system or both can readily identify which type of follicular unit is contained therein. The cartridges may comprise markings, for example color-coding, a unique color used to identify whether the follicular unit is a an F1, F2, F3, etc., or fiducials in the form of a 1-D bar code, a 2-D data matrix code, known markings such as alphanumeric characters, a series of dots, a series of bars, a radio frequency identification (RFID), or any other type of unique identifier or custom scheme. It will be apparent that the location of the markings will depend upon how they are to be utilized, and where they need to be placed in order to be viewed by any applicable image acquisition device.

Figure 3:
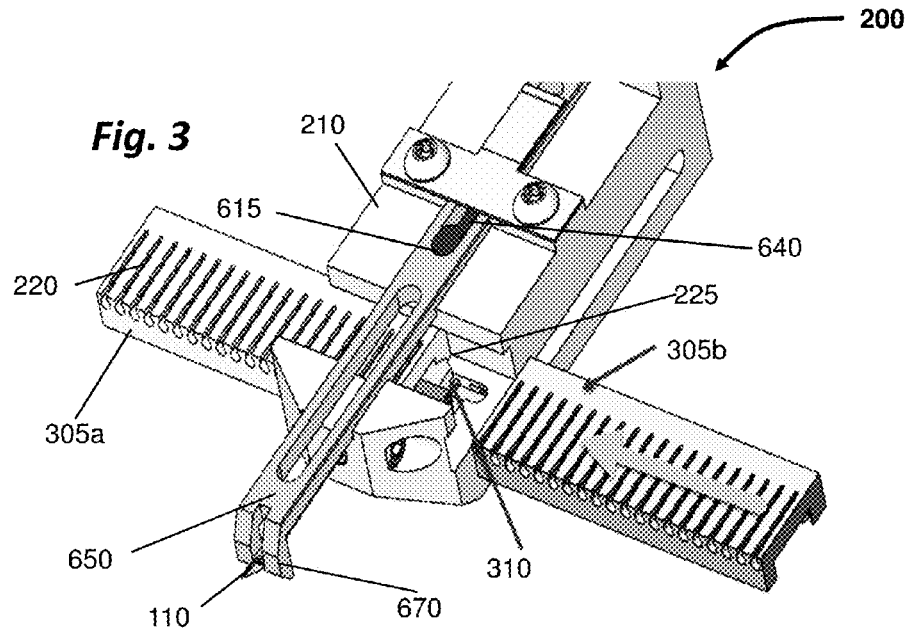
FIG. 3 is a schematic perspective view of an example of a follicular implantation system with two cartridges.
Figure 4:
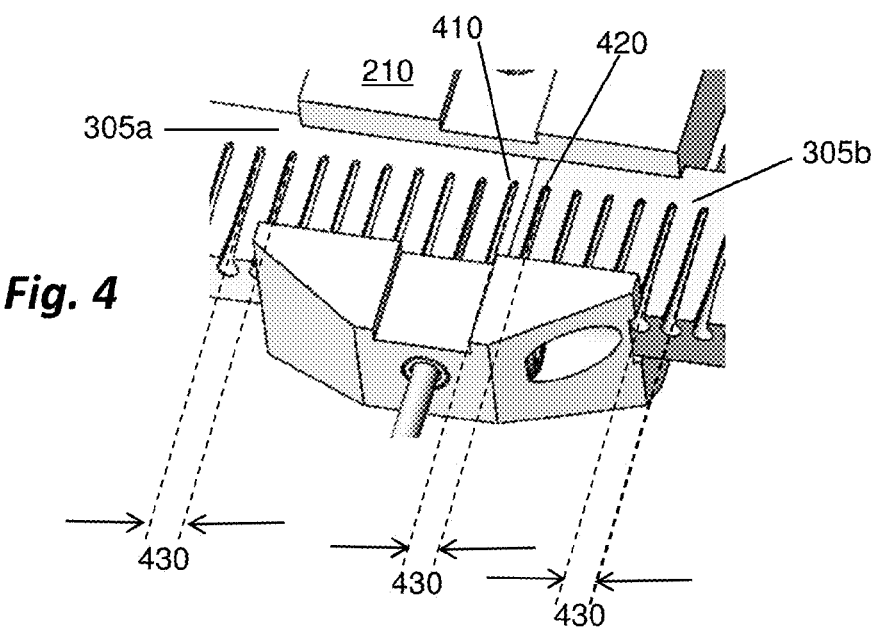
FIG. 4 is a view of two cartridges disposed adjacent one another in an example of a system of the present disclosure.
Figure 5:
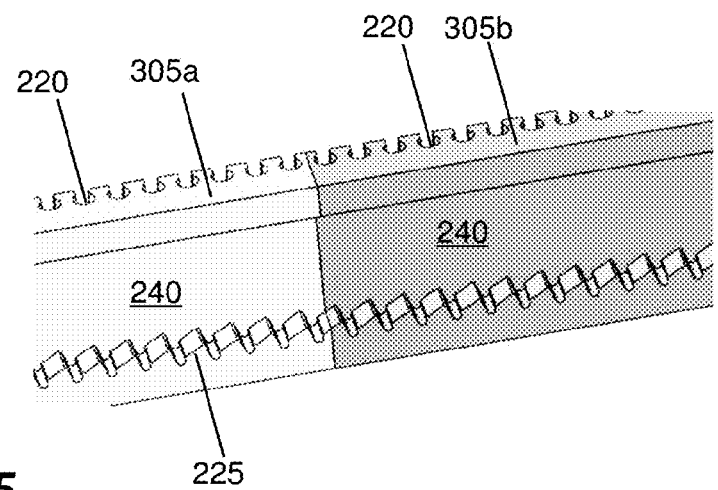
FIG. 5 is a view of the underside of the two cartridges of FIG. 4.

FIG. 3 shows a follicular unit implantation system 200 in which the follicular units have been expelled from a first follicular unit cartridge 305a and illustrates a second follicular unit cartridge 305b being loaded into the tool assembly housing 210. In some embodiments, the system 200 may accommodate more than two cartridges. In the example of FIG. 3, the follicular implantation system 200 includes a follicular unit implantation tool 110, the distal end of which can be seen protruding from a presser foot 650. A drive mechanism, (also not shown) is configured to move or drive an obturator (also not shown) through a receptacle 220 of a cartridge 305a, and into the proximal end of a lumen of the implantation tool 110 to which is substantially aligned. It is desirable that the length of the obturator is such that when the obturator is moved in the distal direction towards the body surface through the receptacle and into the lumen of the implantation tool 110, its distal end may substantially align with the distal end of the tool 110. For that purpose, the length of the obturator may be at least the length of the implantation tool plus the width of the cartridges 305a or 305b, and preferably slightly longer. The drive mechanism may comprise, for example, various motors and other movement devices, and/or may be a part of a control mechanism that may be managed or directed by a processor 125 or a controller 135 shown by example in FIG. 1. The motion of the obturator in a distal direction urges a follicular unit disposed in the receptacle 220 out of the receptacle 220 and into the lumen of the implantation tool 110. The drive mechanism is configured to further drive the obturator toward the body surface, through the implantation tool 110, eventually out of the distal end thereof, and into the body surface 120. Some embodiments, such as the one shown in FIGS. 2-3, may contain a presser foot 650 which is operatively coupled to the obturator and includes a distal end 670. On withdrawal of the obturator from the body surface 120, the distal end 670 of the presser foot 650 depresses the body surface 120 without penetrating it, providing a downward pressure around the obturator, thereby enabling the obturator to be more easily removed from the body surface, and additionally minimizing potential expulsion of nearby previously implanted follicular units, that is providing an anti-popping mechanism. In this particular configuration, when cartridges 305a and 305b are placed end-to-end, the adjacent end faces are substantially parallel to one another. An indexing mechanism 310 is configured such that first and second indexing features 225 on the underside 240 of the respective first and second cartridges 305a and 305b engage with corresponding at least one or more indexing features 320 (shown in FIG. 6a-c and FIG. 7) on an upper portion of the indexing mechanism 310. The indexing features 225 and corresponding indexing features 320 are shaped and configured such that when cartridges 305a and 305b are placed end-to-end (refer to FIGS. 4 and 5), and the indexing features 225, 320 are engaged, the spacing of the last receptacle 410 of the first cartridge 305a and the first receptacle 420 of the second cartridge 305b is a predetermined value 430. The desired distance value between these two receptacles 410 and 420 is such that there is a predetermined spacing 430 between adjacent receptacles, no matter if the receptacles are on the same cartridge or adjacent cartridges. Keeping the distance between receptacles substantially constant between all receptacles, whether they are on the same or adjacent cartridges, enables operation of an obturator (described herein below) to continue without interruption, and automation of the implantation system 200 to be optimized. Optimization is facilitated by, among other things, allowing the obturator to continue urging follicular units from the cartridges at a substantially constant and undisturbed rate; even after all follicular units have been expelled from one particular cartridge. The implantation system 200 is configured such that it provides a seamless, continuous supply of receptacles 220, enabling the implantation of follicular units to continue for as long a cartridges loaded with follicular units are supplied.

In another aspect of the disclosure, the ends of the cartridges may comprise locking features such as, for example, velcro tabs, a dove tail, combination of protrusions and recesses, or other such fastening means which enable one cartridge to be attached to another, end-to-end. Using such an arrangement enables two or more cartridges to be provisionally attached to one another prior to being brought into contact with the indexing mechanism 310.

After one graft from a receptacle has been implanted, the follicular unit cartridge 205 is indexed such that another receptacle, typically an adjacent receptacle, is aligned with the obturator and/or the implantation tool 110, such that a subsequent follicular unit can be implanted. Such indexing may be implemented at least partially automatically, for example, under the control mechanism, such as the controller 135 and/or by other such means, for example a mechanical configuration, a gear arrangement, electro-mechanical, electronic, pneumatic, hydraulic, magnetic, using motors with programmable controls, or a combination thereof for effecting a controlled indexing of the cartridge to preferably align the next receptacle of the cartridge with the obturator. To facilitate indexing, at least one or more indexing features 225 are provided on the lower surface 240 of the cartridge 205 which engage (interlock or mesh) with corresponding at least one or more indexing features 320 (as seen in FIGS. 6a-c) of indexing mechanism 310 associated with the implantation system 200. The indexing features 225 and corresponding indexing features 320 may, for example, comprise a series of teeth, ramps, or leading and trailing edges. An example of a configuration to implement indexing will be described in more detail below, though it will be appreciated that there are many ways of accomplishing this known to those skilled in the art.

FIGS. 6a-6c illustrate an example of an indexing mechanism 310 which may be implemented with various embodiments according to another aspect of the disclosure. The indexing mechanism 310 comprises not only corresponding indexing features 320 which engage with indexing features 225 on the underside 240 of the cartridge 205, but a cam surface 330 which is configured to operate in association with an indexing cam 610. In the configuration described, the corresponding indexing features 320 are disposed on an upper surface of the index mechanism 310, the surface closer to the loaded follicular units, and the cam surface 330 is disposed on a lower surface of the index mechanism 310, the surface furthest from the loaded follicular units. The obturator 550 is slidably positioned, with its proximal end coupled via an indexing cam 610 to a drive mechanism (not shown) driven by a drive assembly (also not shown) for providing a distally-directing urging force on the obturator 550. In operation initially, as illustrated by FIG. 6a, the cartridge 205 is engaged with the indexing mechanism 310, and the drive mechanism activated to retract the indexing cam 610 as shown, substantially simultaneously causing the obturator 550 to retract. In this retracted position, protrusion 615 of the indexing cam 610 is disposed at a proximal end 630 of slot 640, additionally causing the presser foot 650 to be retracted, and thereby retracting the distal end 670 of the presser foot 650 from the body surface 120. For purposes of the description of FIGS. 6a-c, the "distal" direction is the one closer to the body surface 120 and the "proximal" direction is away from the body surface 120. When the obturator 550 is retracted, the index mechanism 310 is in its biased position, biased by means of a spring or other such biasing component (not shown) in the directions 710 and 720 as shown in FIG. 6a. It should be understood that various modifications, substitutions and changes in the form and details of the configuration described and in the operation of the described instruments and systems can be made without departing from the spirit of the disclosure. For example, in alternative embodiments, the indexing features 225 of the cartridge and the indexing features 320 on the indexing mechanism 310 may be disposed at other locations (for example, on the other side of the respective devices), also the initial biasing may be in the directions other than those indicated above, and/or the movement of the obturator may cause the indexing mechanism and/or the cartridge to move in a direction other than that described (e.g., opposite). Subsequently, the drive mechanism provides a distally-directed motion causing indexing cam 610 to move toward the cartridge 205, and moving the distal end of the obturator 550 through a receptacle 220 in the cartridge 205 to which the obturator 550 has been substantially aligned. The indexing cam 610 is configured such that when the protrusion 615 reaches the distal end 660 of slot 640, the distal end of the obturator 550 is substantially aligned with the distal end 670 of the presser foot 650 (FIG. 6b).

As the drive mechanism continues to move the indexing cam 610 towards the cartridge 205, the disposition of the protrusion 615 in the slot 640 causes the protrusion 615 to move the presser foot 650 and the obturator 550 in a distal direction toward the body surface 120. The cam surface 620 of the indexing cam 610 engages the cam surface 330 disposed on a lower surface of the index mechanism 310 and urges the indexing mechanism 310 to its cocked position, urging it to move in a direction 700 shown in FIG. 6c. However, since the obturator 550 is in the receptacle 220 of the cartridge 205, the indexing mechanism 310 is limited in how far it is able to move in the direction it is being urged. This motion can be seen more clearly in FIG. 8, in which it can be seen that as the cam surface 620 of the indexing cam 610 moves towards the body surface 120 and slides across the cam surface 330 of the indexing mechanism 310, the indexing mechanism 310 is urged in direction 700, and also urged in the distal direction 730, towards the body surface 120. The system is configured such that due to the positioning of the obturator 550, the cam arrangement, the geometry of the indexing features, and biasing, the indexing mechanism 310 is moved a distance sufficient to increment a corresponding indexing feature 320 on the indexing mechanism 310 to the adjacent indexing feature 225 on the cartridge 205. The geometry of the indexing features 225 contributes to ensuring that once moved a distance sufficient to implement indexing, the corresponding indexing features 320 of the indexing mechanism 310 fall or drop into place with respect to the indexing features 225 of the cartridge 205, prior to the index mechanism 310 moving back towards it biased position, thus making sure that indexing occurs. During this time, the drive mechanism is controlled in such a manner as to cause the obturator 550 to urge a follicular unit from the receptacle 220 of the cartridge 205, into the lumen of the implantation tool 110, out of the distal end of the implantation tool 110 and into the body surface 120. By controlling the distal end 670 of the presser foot 650 to reach the surface of the body surface 120 without penetrating it, and by substantially aligning the distal end of the obturator 550 with the distal end 670 of the presser foot 650, a desired depth of implantation can be achieved and controlled. In such embodiment, neither the distal end 670 of the presser foot nor the distal end of the obturator 550 penetrates the body surface 120.

Figure 8:
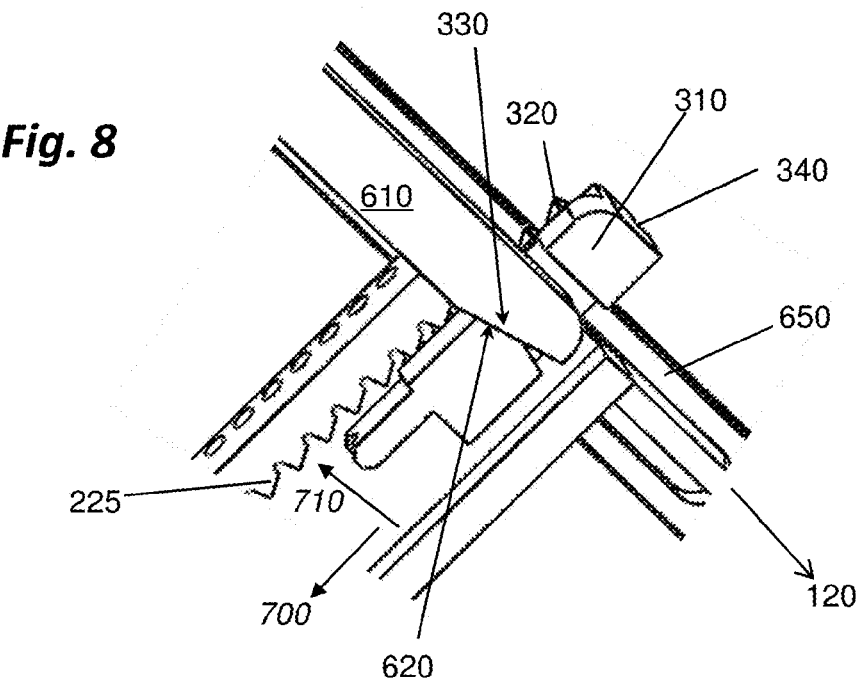
FIG. 8 illustrates an example of the underside of the indexing mechanism comprising a cam surface that can be implemented in various embodiments of the disclosure.

Once the follicular unit is implanted, the drive mechanism (or control mechanism) causes the indexing cam 610 to be retracted together with the obturator 550, moving them both in the proximal direction, away from the body surface 120. In some embodiments, the drive mechanism may be actuated by one of the processors (such as those described in FIG. 1 in reference to one or more processors 125). Initially the retraction is such that the presser foot 650 remains stationary, and only the obturator 550 is retracted in the proximal direction. However, once retracted sufficiently, the protrusion 615 of the indexing cam 610 reaches the proximal end 630 of the slot 640, and the presser foot 650 is retracted along with the obturator 550. Maintaining contact initially between the distal end 670 of the presser foot 650 and the body surface 120, as the obturator 550 is retracted from the body surface 120 may serve to optimize the implantation of the follicular unit. Eventually, the obturator 550 is retracted out of the receptacle 220 of the cartridge 205 allowing the indexing mechanism 310 to be released back to its biased position, that is in the direction 720 (referring to FIG. 6a)(opposite to direction 700). In addition, as the obturator 550 has been retracted from the cartridge 220, the indexing mechanism 310 is also able to return to its biased position which is in a proximal direction 710 (FIG. 6a) away from the body surface 120, and the cartridge 220 indexes such that an adjacent receptacle is substantially aligned with the obturator 550, and the process ready to begin again. The indexing mechanism 310 further comprises a stop 340 which limits the movement of the indexing mechanism 310 as it returns to it biased position, which in turn ensures that the indexing is limited to incrementing to the adjacent receptacle. As illustrated in FIG. 8, the stop 340 may comprise the end of the indexing mechanism 310, with a recess in the tool assembly housing 210 providing a stop boundary 680. In this manner, the ability of the indexing mechanism 310 to move is limited in the directions 700 and 720.

As mentioned earlier, utilization of the presser foot 650 while withdrawing the obturator from the body surface 120 enables the obturator to be more easily removed from the body surface, and additionally minimizes potential expulsion of nearby previously implanted follicular units, providing an anti-popping mechanism. The distal end 670 of the presser foot 650 depresses the body surface 120 without penetrating it, providing a downward pressure around the obturator, and effectively stabilizing the body surface area surrounding it. Thus when the obturator is removed, there is less disturbance within the area surrounding the obturator, minimizing potential expulsion of nearby previously implanted follicular units.

The utilization of a presser foot 650 in combination with the obturator 550 may be particularly useful in hand-held devices, in which the axial position of the obturator may not be readily apparent to the user, as it may be concealed within the lumen of the needle. The presser foot 650 may provide a visual indication by which the user can judge how far a needle is being penetrated into the body surface and may also act as a stopper for the obturator.

It should be understood, however, that in some embodiments, the use of the presser foot is optional. For example, in some embodiments, the processor or controller of the system may control the distance that the obturator moves without the use of a presser foot. The image acquisition device 115 may acquire data pertaining to the distance of the implantation tool and/or the obturator relative to the body surface, and the processor and/or controller of the system may control the distance that the implantation tool and/or the obturator moves, including, when desired, preventing the obturator from penetrating the body surface.

Figure 9:
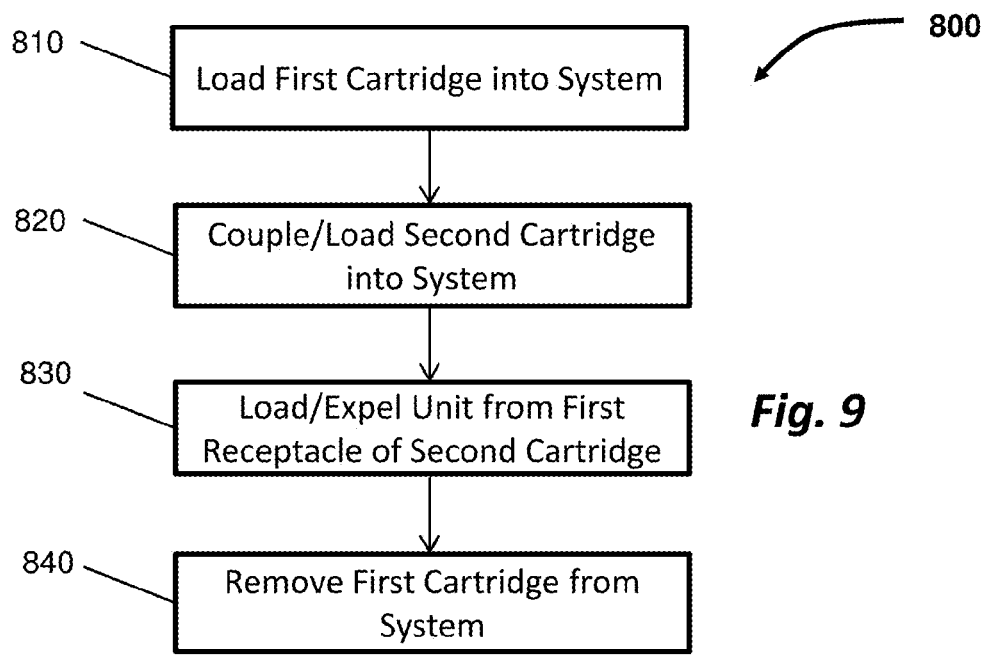
FIG. 9 shows a flow diagram of an example of methodology according to an aspect of the disclosure.

FIG. 9 is a flow diagram describing an example of methodology for a continuous feed of receptacles using systems and instruments of the present disclosure. In a preliminary step 810, a first cartridge 220 comprising a plurality of receptacles may be loaded into the system, the adjacent receptacles of the plurality of receptacles are separated from each other by a predetermined distance. The system may be operated to either load objects or units into or expel objects or units out of the receptacles of the first cartridge. The loading or expelling may comprise operating an obturator (or other similar mechanism) to move into or enter the receptacle, pushing an object or unit (such as, a hair graft) either into or out of the receptacle, depending upon the application. In other implementations, the loading or expelling may be accomplished by using a pressure differential to urge the object or unit out of each receptacle and into the tool 110, as further described below. In further implementations, for example, a combination of mechanical pushing and pressure differential could be used to expel the follicular unit from the cartridge.

The movement of the obturator or similar mechanism may be controlled by one or more processors 125. At some point during the procedure, in step 820, a second cartridge may be operatively coupled to the system, for example, by locking the second cartridge to the first cartridge. In some embodiments, to keep the overall dimensions of the system to a minimum during the most of its operation, the second cartridge may be coupled shortly before all or almost all of the receptacles of the first cartridge are emptied (in reference to the implantation procedures) or filled with the objects (in reference to loading of the receptacles of the cartridge with the objects). For example, the second cartridge may be coupled when the system is about to expel the follicular unit from the last receptacle of the first (or previous) cartridge. In those embodiments, the time during which both the first and the second cartridges are loaded in the system is minimized. However, in other implementations, the second cartridge may be coupled at any other desired or appropriate time. It should be understood that the "last" receptacle in the first cartridge may not be an actual physical last receptacle, but may be the last one on which a loading or expelling operation was instructed by the system, the last receptacle from which an object or unit was expelled or into which an object or unit was loaded in the first (or previous) cartridge before commencing operation on a second (or subsequent) cartridge is desired. In step 830, the system is operated to either load objects or units into or expel objects or units out of the first receptacle of the second cartridge. According to the methodology of the present disclosure, objects or units can be loaded into or expelled from a first receptacle of the second cartridge without losing any time by interrupting the procedure to remove the previous cartridge and replace it with the subsequent one. In some embodiments, step 830 may be performed while the first (previous) cartridge remains operatively attached to the system and in step 840 the first cartridge may be removed any time after an object, such as follicular unit is being expelled from the first receptacle of the second cartridge. If desired, in some implementations, several or more receptacles of the second (or subsequent) cartridge may be emptied before the first cartridge is disconnected or removed from the system. In other embodiments, steps 830 and 840 may be performed substantially simultaneously, such that loading of objects into or expelling objects from a first receptacle of the second cartridge may take place at a substantially the same time as the first cartridge is being removed or disconnected from the system. In either case, the removal of the first cartridge from the system does not impact efficiency of loading/expelling, as it does not prevent the procedure from continuing to allow objects or units to be loaded into or expelled from the receptacles of the subsequent cartridge at the same rate and without interruptions.

Figure 7:
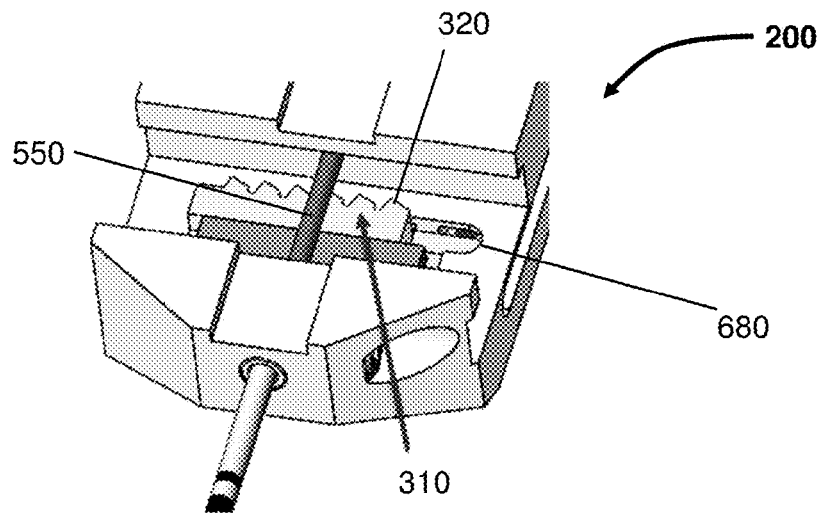
FIG. 7 illustrates an example of an upper portion of the indexing mechanism comprising corresponding indexing features according to the disclosure.

Moreover, in some embodiments of the disclosure, the system may be configured to recognize and/or indicate when the work on a previous cartridge is completed or about to be completed, and direct coupling of the subsequent cartridge. One or more indicators, for example fiducials, may be placed adjacent an end of the first cartridge and utilized to provide an indication to the user or the system that the last receptacle of the first cartridge is being or close to being emptied or filled. This information, for example, may be displayed on the display device 140, indicating that the user should soon remove the first cartridge, or may be used by the system to provide automatic removal/disconnection of the first cartridge. In an alternative embodiment, the length of the indexing mechanism 310 may facilitate automatic disconnection of the first cartridge. As illustrated in FIG. 7, it can be seen that the indexing mechanism 310 comprises a finite length with a finite number of indexing features 320. Therefore once the first cartridge 305a has been indexed in a step-wise fashion, eventually the first indexing features 225 of the first cartridge 305a will no longer engage with the corresponding index features 320 of the indexing mechanism 310. Therefore as the second cartridge 305b also indexes, there will be a point in time in which only the second cartridge 305b is engaged with the corresponding index features 320 of the indexing mechanism 310, and the first cartridge 305a will be automatically disconnected therefrom. It will be apparent that selection of a particular length of indexing mechanism 310 will determine the disconnection time.

Cartridges for Use with the Systems and Methods of the Present Disclosure

Figure 10:
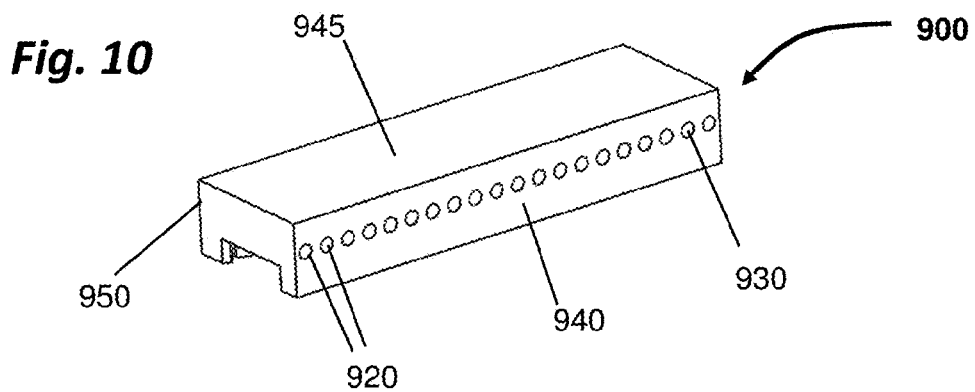
FIG. 10 illustrates an example of a linear follicular unit cartridge of a prior art.

According to another aspect of the present disclosure, improvements in the design and configuration of the cartridge itself are provided. The cartridge configurations described may be utilized in automated or semi-automated procedures, including with the robotic systems. In addition, such cartridge configurations may be utilized using, for example, a hand-held device, even though such device or a procedure may be automated to various degrees. As explained above, the cartridge may have a plurality of receptacles for containing various biological units (such as hair grafts or tissue grafts) that must be stored and removed from such receptacles without damaging such grafts so that they can be, for example, implanted or reused. FIG. 10 illustrates a cartridge 900 similar to a cartridge disclosed in the commonly assigned U.S. Pat. No. 8,211,134, for example, in FIG. 18, in which the receptacles 920 are disposed within the body of the cartridge 900 spaced from the top surface of the cartridge 945. In other words, an opening or a bore 930 of the receptacle 920 extends from a first or front face 940 to a second or rear face 950 (not shown) which is substantially parallel to the front face 940, with no portion of the length of the receptacles being exposed to the top surface 945. In this particular configuration, the follicular units may be loaded into the cartridge by pushing one graft (e.g., follicular unit) into each opening 930 of the receptacles 920 with no portion of follicular unit exposed on the surface of the cartridge 900.

Figure 11:
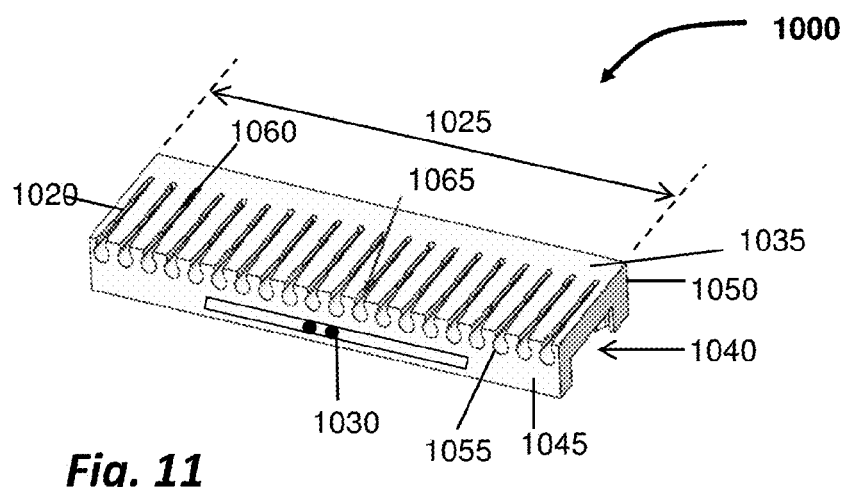
FIG. 11 illustrates a linear follicular unit cartridge according to various embodiments of the present disclosure.

FIG. 11 illustrates a cartridge 1000 according to the present disclosure. The cartridge 1000 includes a body having a first or top surface 1035, a second or bottom surface 1040, a front face 1045 and a rear face 1050 (not shown), and defining a plurality of receptacles 1020 running substantially parallel from the front face 1045 to the rear face 1050. In the illustrated example, cartridge 1000 comprises twenty (20) receptacles 1020, each sized and configured to retain a follicular unit. It should be understood, however, that this is an example only and a different number of receptacles is within the scope of the present disclosure. The length 1025 of the cartridge 1000 in the example of FIG. 11 has been selected such that it can easily be stored in a petri dish until required, the length 1025 being in the range of 2 to 10 cm in length, with a length of 3 to 3.5 cm, and more specifically, 3.2 cm, for example, easily accommodating the 20 receptacles illustrated. The receptacles 1020 are configured such that they are disposed closer to the top surface 1035, for example, within 0.2 mm to 0.5 mm from the top surface 1035.

Figure 12:
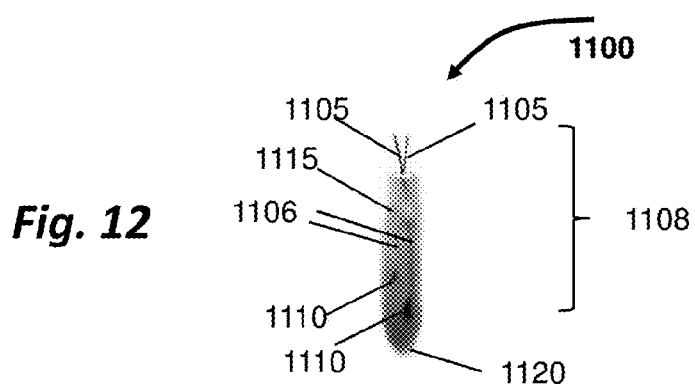
FIG. 12 illustrates a follicular unit.
Figure 13:
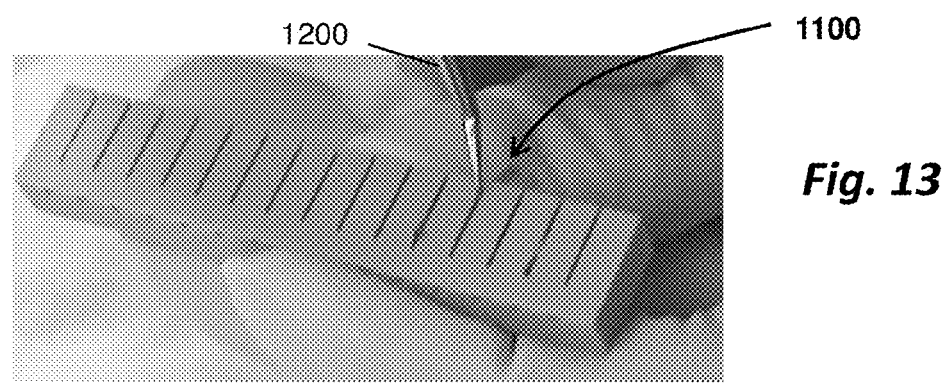
FIG. 13 shows a follicular unit being loaded into the linear cartridge, such as the cartridge of the example of FIG. 11.

In this particular example, slots 1060 extend from the receptacles 1020 and open to the top surface 1035 of the cartridge 1000. These slots 1060 aid in the process of loading follicular units into the receptacles 1020 of the cartridge 1000. In certain implementation, the grafts or follicular units may be placed into receptacles with the use of the forceps. Slots 1060 allow for guiding the forceps as the follicular unit is pulled through the first opening 1055 and into the receptacle 1020. Additionally, the slots 1060 may be tapered (e.g., widened) towards the first opening 1055 of the receptacle 1020, the tapered portion providing an additional guide feature 1065, that may, for example, further accommodate the forceps as they introduce the follicular unit into the first opening 1055, without subjecting to any unnecessary trauma the follicular unit being loaded. This configuration enables the user to load the cartridge with follicular units faster and/or easier than in a configuration which does not comprise slots 1060 or additional guide features 1065. To aid in the understanding of how follicular units are loaded into a cartridge, reference is made to FIGS. 12 and 13. FIG. 12 depicts a follicular unit or hair graft 1100 comprising of one or more hair follicles or hair shafts 1108, each extending from a corresponding bulb 1110, the follicular unit 1110 having a distal end 1120 positioned beneath the skin. Typically, the hair bulb 1110 and a portion 1106 of the hair shaft 1108 are surrounded by tissue 1115 wherein a tip portion 1105 of the hair shaft 1108 being free of any tissue and representing a portion of the hair follicle or hair shaft that emerges from the body surface. This tip portion 1105 is usually trimmed to about 1 mm to 2 mm (0.04 to 0.08 inches) when hair transplantation is performed using hand-held instruments or during an automated (e.g., robotic) follicular unit extraction procedures, and it is typically trimmed to about 3 mm to 5 mm (1.12 to 1.16 inches) when a strip hair transplantation procedure is performed. The stem cells responsible for the growth of hair are typically located along the portion 1106 of the hair follicle 1108 that is below the epidermis down through the hair bulb 1110. As shown in FIG. 13, the user guides a follicular unit 1100 held by the tip portion 1105 with a pair of forceps 1200 or a similar device into the slot (typically starting at the first opening 1055) into the receptacle 1020 (shown in FIG. 11). In some embodiments, the slots 1060 may traverse the width of the cartridge 1000. In other embodiments, such as that illustrated, the slot may traverses only a portion of the width of the cartridge 1000 (in some instances a substantial portion), but ends before reaching the rear face 1050. In this manner, the user is able to hold, with the aid of forceps, the tip portions 1105 of a follicular unit 1100 (refer to FIG. 12) without squeezing and potentially damaging the portion that contains the stem cells and surrounded by tissue 1115, and pull the follicular unit 1100 into first opening 1055, through the receptacle 1020 until an end of the slot 1210 furthest from the first opening 1055 is reached. At this point, the tissue portion 1115 of the hair graft will be disposed substantially within and along the receptacle 1020, with the distal end 1120 of the follicular unit 1100 disposed at or near the first opening 1055, and with the ends of the tip portions 1105 protruding from the other end 1210 of the slot, as best seen in FIG. 14.

Another feature of the cartridge of the present disclosure provides for convenient marking to inform the user or the automated system what type of biological units it contains. For example, in reference to hair implantation, the cartridges may be marked to indicate the number of hair follicles in the respective follicular units contained in a particular cartridge. The illustrated series of dots 1030, may serve to show one example of how the cartridge 1000 containing type F2 follicular units may be marked.

Once the cartridge has been loaded with follicular units, it can be inserted into the follicular unit implantation system 200 to implant follicular units into the patient's body surface 120. Movement of the hair follicles from the receptacles 1020 of the cartridge 1000 to the implant tool 110 may be accomplished using various approaches. The follicular unit 1100 may be pushed from the cartridge 1000 into the implant tool 110 using, for example, a mechanical device such as obturator 550. The operator or system may translate the obturator 550 through a portion or the full length of the receptacle 1020, thus pushing the follicular unit 1100 out of the receptacle 1020 and into the lumen of the tool 110, which is positioned to be substantially aligned with the receptacle 1020. The reader should understand that transferring of follicular units from the cartridge to the implantation tool could be accomplished using several alternative approaches. Another option is to use a pressure differential to urge the follicular unit out of each receptacle and into the implantation tool 110. In other alternative embodiments, a combination of mechanical pushing and pressure differential could be used to expel the follicular unit from the cartridge.

Obturators for Use with the Systems and Methods of the Present Disclosure

According to yet another aspect of the present disclosure, FIGS. 14-17 illustrate a new and improved design of an obturator 1150 that can be used with the system and methods of the present disclosure. Typically, the obturators for use in hair transplantation may have a diameter of approximately 0.8 mm to 1.1 mm (or approximately 0.03 to 0.04 inches). In reference to hair transplantation, the obturator 1150 is sized, shaped and configured such that it accommodates the tip portions 1105 of the one or more hair follicles 1108 which protrude from the tissue 1115 and improves successful guiding of the hair graft or follicular unit 1110 into the tool when the obturator 1150 pushes the follicular unit 1100 out of the receptacle 1020. For that purpose, the distal end of the obturator 1150 comprises a recess 1155 disposed in the first (e.g., top) side 1180 therein. The recess 1155 is sized and configured such that the tip portions 1105 are able to lay or reside within the recess 1155, such that they are not caught or pinched when the graft is being expelled by the obturator from the receptacle of the cartridge into the tool 110. There is some tolerance between the outside diameter of the obturator 1150 and the internal diameter (or lumen walls) of the implantation needle 110, or the internal diameter of the receptacles 220 of the cartridge 205. Nominally, the tolerance may be between about 0.025 mm and 0.05 mm (or between about 0.001 and 0.002 inches.) Regular tip portions 1105 of the hair has a nominal diameter of 0.1 mm or 0.004 inches, but it is not uncommon for miniature hairs to have a diameter of less than 0.05 mm or 0.002 inches. Therefore without the recess 1155, there is a possibility that the tip portions 1105 of the hair may be pinched between the internal diameter of the implantation needle 110 and the outside diameter of the obturator 1150, or between the internal diameter of the receptacles 220 of the cartridge 205 and the outside diameter of the obturator. There is also a possibility that the tip portions 1105 of the hair may get pinched when traveling from the receptacle 220 of the cartridge 205 to the implantation needle 110, as it has to overcome a small gap between the two. The recess, such as recess 1155 on the top side at the distal end of the obturator 1150 provides a pocket for the hair. For example, in the embodiments where the units to be stored in the cartridge are hair grafts, the length of the recess 1155 may be approximately 1.5 mm to 2.5 mm (0.06 to 0.1 inches) (to accommodate the length of 1 to 2 mm (0.04 to 0.08 inches) of the tip portions 1105). The depth of the recess 1155 may be, for example, 0.2 mm to 0.3 mm (0.008 to 0.012 inches) (which accommodates comfortably a caliber of the one or more tip portions 1105 of the follicular unit 1110), or in a range of about 10 percent to about 30 percent, for example, 25 percent, of a cross-sectional dimension of the elongated body of the obturator. As will be understood by those skilled in the art, the dimensions of the recess 1155 above are provided by way of example, and are not limiting and can be adjusted depending on desired implementation and application. In this configuration, when the distal tip 1160 of the obturator 1150 pushes on the portion of the graft surrounded by tissue 1115, the tip portion 1105 which protrudes from the tissue 1115 is not bent, pinched or caught as explained above, preventing the graft from being properly aligned and smoothly transferred from the storage cartridge into the tool 110. In one embodiment of the current disclosure, the obturator 1150 advances through the receptacle 1020 to which it is aligned, urging the follicular unit 1100 contained therein to be expelled from the receptacle 1020 and to enter a proximal end of the lumen of the implantation tool 110. The implantation tool 110 is operated to cause the distal end of the implantation tool 110 to enter the body surface 120. To accomplish this, the distal end of the implantation tool 110 may be sharpened so that the tool itself penetrates the body surface, or, alternatively, the tool may be introduced into a previously formed puncture or incision (made by another instrument). It will be appreciated that penetration of the body surface may occur prior to, during or after the time in which the follicular unit is expelled from the receptacle 1020 and into the lumen of the implantation tool 110. It will also be appreciated that the methods by which the follicular units 1100 are caused to move from the cartridge 1000 to the implantation tool 110 can be accomplished by various approaches, other than those described above.

Figure 16A:
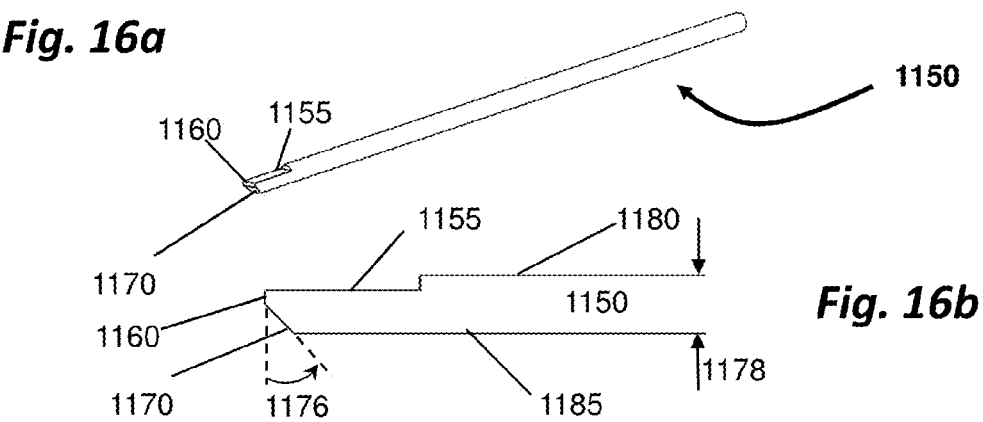
FIGS. 16a-b show schematic representations of the obturator of FIGS. 14 and 15.
Figure 16B:
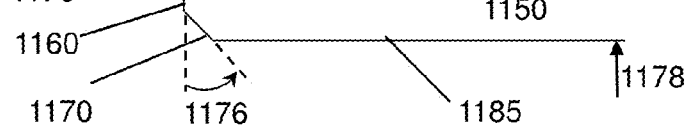
Figure 17A:
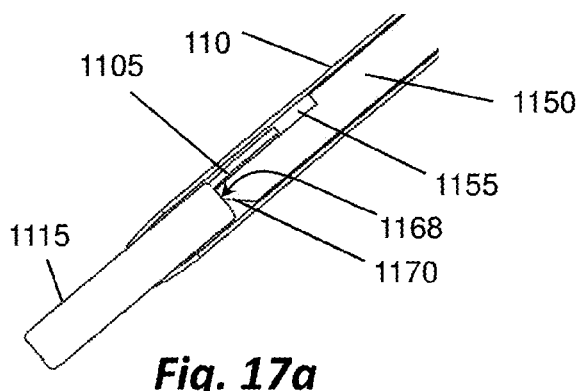
FIG. 17a-b show a follicular unit being expelled from a tool.
Figure 17B:
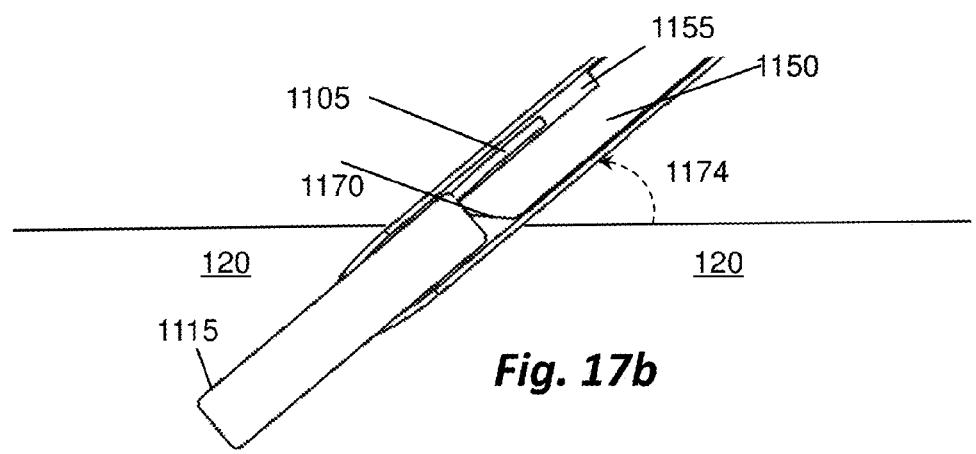

Additionally, in some embodiments the obturator 550 of the present disclosure may be configured with a cut-out portion 1170, disposed at the distal tip of the obturator 550, but on a second (e.g., bottom) or opposite side 1185 from the recess 1155 (see FIGS. 16a-16b). The cut-out portion 1170 may be configured such that in use, when the distal end of the implantation needle 110 penetrates the body surface 120 at an approach angle denoted as 1174 in FIG. 17b, the surface of the cut-out portion 1170 of the obturator 1150 lies substantially parallel to the body surface 120. In this manner, when the distal tip 1160 of the obturator 1150 pushes the proximal end 1168 of the portion of the graft surrounded by tissue 1115, the surface of the cut-out portion 1170 is substantially aligned with the body surface 120 preventing the obturator 1150 from entering below the body surface 120, as shown in FIG. 17b. At the same time, the distal tip 1160 of the obturator 1150 is able to exert sufficient force over the area of the distal tip 1160 to push the follicular unit to the desired position to result in implantation. To perform a hair implantation procedure, the implantation needle 110 may be advanced at an approach angle anywhere in the range of 30-90 degrees with respect to the body surface, though a more typical range of approach angle is between 40-45 degrees. Therefore to place the cut-out portion 1170 of the obturator 1150 substantially parallel to the body surface (when the obturator 1150 is in use, and utilizing an approach angle to penetrate a body surface), the cut-out portion 1170 is configured to form an angle (denoted as 1176 in FIG. 16b) in the range of 0-60 degrees, and typically between 45-50 degrees. In some embodiments, the cut out portion may pass through the whole or a portion of the diameter of the obturator. In such embodiments, the distal tip 1160 and the cut-out portion 1170 intersect at a line which is formed substantially across a diameter of the obturator 1150, the cut-out portion 1170 initiating at approximately along a line passing through a diameter of the obturator, or close thereto. As mentioned earlier, the diameter 1178 of the obturator 550 may be in the region of 0.8-1.1 mm (0.03 to 0.04 inches). In some other embodiments, the cut-out portion 1170 may extend from about 25 percent to about 60 percent, for example, 50 percent, of a cross-sectional dimension of the obturator 1150, for example such that only a portion of the cross-section of the distal tip of the obturator that positioned closer to the body surface is cut out. The cut-out 1170 is configured and functions such that when the obturator is pressed against the body surface 120, the cut-out is substantially flush with the surface of the body surface, thereby enabling the distal end of the obturator to not substantially compress the body surface.

In some embodiments, the distal end of the obturator 1150, the end which comes into physical contact with the follicular unit, additionally may comprise a non-traumatic surface, which is preferably not able to damage the hair graft when it pushes against the hair graft portion 1115. On the other hand, in some alternative embodiments that do not have a recess 1155, such as those shown in the embodiment of FIGS. 16-17, at least a portion of the distal tip of the obturator 1150 may have a sharp cutting edge. The purpose of such cutting edge is to assist in smooth transitioning of the graft into the tool 110 by being able to cut the tip portions 1105 which may be caught between the outside diameter of the obturator and the inside diameter of the cartridge 205, or between the outside diameter of the obturator and the inside diameter of the implantation needle or tool 110.

Alternatively, other urging mechanisms or means for urging the follicular unit through the implantation tool may be utilized. For example, a pressure differential, as mentioned above, may be applied to the implantation tool lumen by reducing the pressure at the distal end of the receptacle relative to the proximal end. One example of such pressure is the pressure that is caused by a very small volume of saline that has been pushed from the tip of a tubular obturator (for the embodiments where the saline is used).

FIG. 18 illustrates an example of a hand-held instrument 1200 for implanting hair grafts into a body surface. Hair grafts are loaded into a plurality of receptacles of cartridge 1210, which may be configured to be releasably connected to the body 1220 of the hand-held instrument 1200, for example, via a release mechanism 1230. The release mechanism 1230 may comprise, for example, two outwardly directed and diametrically arranged biased, or spring loaded protrusions, which engage an inwardly directed recess on an inner wall of the cartridge 1210. Twisting or turning of the cartridge 1210 urges the protrusions to release the cartridge 1210 from or to lock the cartridge to the body 1220 of the hand held tool. Other mechanisms that may selectively lock and release cartridges from bodies are known to those in the art, and therefore will not be described. In use, a plunger 1240 may be activated (e.g., by the user or automatically), which operates an obturator or other urging mechanisms (not shown) to urge a follicular unit from the cartridge 1210, into the implantation tool 1250, and out of the distal end thereof. The plunger 1240 can also activate the presser foot. On retraction of the obturator (or e.g., release of the pressure differential), the cartridge is indexed and an adjacent follicular unit in the cartridge aligned for implantation. Though illustrated with a circular cartridge, the hand-held cartridge may comprise a linear cartridge including one or more of the novel features described above.

The various embodiments described above are provided by way of illustration only and should not be construed to limit the claimed disclosure. These embodiments are susceptible to various modifications and alternative forms, and it should be understood that the invention generally, as well as the specific embodiments described herein, cover all modifications, equivalents and alternatives falling within the scope of the appended claims. By way of non-limiting example, it will be appreciated by those skilled in the art that particular features or characteristics described in reference to one figure or embodiment may be combined as suitable with features or characteristics described in another figure or embodiment. For example, when used in combination with a "long" cartridge, the use of fiducials may serve as unique identifiers for the type of follicular unit contained in a cartridge containing similar follicular unit types in pre-assigned portions of the cartridge. The unique identifiers may subsequently be recognized by an imaging acquisition device associated with the robotic and implantation systems, such that the indexing mechanism indexes the cartridge such that the required follicular unit type is aligned with the tool for implantation into the body surface. This particular configuration requiring the indexing mechanism to be able to index the cartridge both backwards and forwards, and not in a singular direction as described above. Further, those skilled in the art will recognize that the devices, systems, and methods disclosed herein are not limited to one field, such as hair restoration, but may be applied to any number of fields. The description, therefore, is not to be taken in a limiting sense, and the scope of the present disclosure is defined by the appended claims. It will be further appreciated by those skilled in the art that the disclosure is not limited to the use of a particular system, and that automated (including robotic), semi-automated, and manual systems and apparatus may be used for positioning and actuating the respective tools and other devices and components disclosed herein.

What is claimed is:

1. A hair transplantation apparatus comprising:
   a first cartridge having at least one first indexing feature and comprising a first plurality of receptacles with a predetermined spacing therebetween, each receptacle sized and configured to retain a follicular unit;
   a second cartridge having at least one second indexing feature and comprising a second plurality of receptacles with the predetermined spacing therebetween, each receptacle sized and configured to retain a follicular unit;
   wherein the first cartridge and the second cartridge each comprises an elongated substantially linear body with end faces and with the corresponding first or the second plurality of receptacles disposed to extend from a front face to a rear face of the corresponding first or second cartridge and to be substantially parallel to each other;
   a housing configured to accommodate one or more cartridges;
   an urging mechanism operative when substantially aligned with one of the first plurality of receptacles of the first cartridge or one of the second plurality of receptacles of the second cartridge to load the follicular unit into the one of the first plurality of receptacles of the first cartridge or into the one of the second plurality of receptacles of the second cartridge or to expel the follicular unit from the one of the first plurality of receptacles of the first cartridge or from the one of the second plurality of receptacles of the second cartridge; and
   an indexing mechanism comprising indexing features configured to simultaneously engage with the at least one first indexing feature of the first cartridge and the at least one second indexing feature of the second cartridge when the first cartridge and the second cartridge are placed end-to-end and to simultaneously move the first cartridge and the second cartridge in the same direction to align a receptacle of the first or the second plurality of receptacles with the urging mechanism;
   wherein the apparatus is configured to operatively couple the first cartridge to the second cartridge such that a distance between a last receptacle of the first plurality of receptacles of the first cartridge and a first receptacle of the second plurality of receptacles of the second cartridge equals the predetermined spacing and wherein the urging mechanism is configured to move into alignment with the first receptacle of the second plurality of receptacles of the second cartridge without disconnecting the first cartridge from the apparatus.

2. The apparatus of claim 1, the apparatus configured to automatically disconnect the first cartridge substantially at the time or after at least one follicular unit is expelled from or loaded into the first receptacle of the second cartridge.

3. The apparatus of claim 1, wherein the urging mechanism comprises an obturator sized and configured to pass through a selected receptacle of the first plurality of receptacles of the first cartridge or of the second plurality of receptacles of the second cartridge.

4. The apparatus of claim 3, wherein the obturator comprises a recess configured to accommodate one or more tip portions of the follicular unit.

5. The apparatus of claim 3, wherein the apparatus is configured such that retraction of the obturator from the selected receptacle causes the first and second cartridge to index.

6. The apparatus of claim 3, wherein the obturator comprises a cut-out portion disposed at a distal tip of the obturator and at an angle to the distal tip.

7. The apparatus of claim 1, wherein the at least one first indexing feature, the at least one second indexing feature, and the indexing features of the indexing mechanism comprise one or more teeth.

8. The apparatus of claim 1, the apparatus comprising an indicator configured to inform when the last receptacle of the first cartridge has been or is about to be emptied or filled.

9. The apparatus of claim 1, the apparatus configured to couple the first and second cartridges to each other when placed end-to-end.

10. The apparatus of claim 1, wherein at least one receptacle of the first and/or the second plurality of receptacles contains a follicular unit preservation solution.

11. The apparatus of claim 1, wherein at least one of the first cartridge or the second cartridge comprises fiducials configured to indicate: 1) a type of follicular unit contained therein, and/or 2) whether an end of the cartridge has been reached.

12. The apparatus of claim 1, further comprising a robotic hair transplantation system, wherein the apparatus is configured to be removably received in the robotic hair transplantation system, robotic hair transplantation system comprising a robotic arm, a control mechanism, and an implanting tool having a lumen therethrough and being connected to and manipulated by the robotic arm; and wherein the control mechanism is adapted to automatically align a selected receptacle of the first plurality of receptacles of the first cartridge or of the second plurality of receptacles of the second cartridge with the lumen of the implanting tool and urge the follicular unit from the selected receptacle through the lumen of the implanting tool into a body surface.

13. The apparatus of claim 12, wherein the robotic hair transplantation system further comprises an obturator positioned to pass through a selected receptacle of the first or the second cartridge to urge the follicular unit therefrom.

14. The apparatus of claim 12, wherein the robotic hair transplantation system further comprises a pressure differential through the selected receptacle, and wherein the control mechanism initiates a pressure differential through the selected receptacle to urge the follicular unit from the selected receptacle.

15. The apparatus of claim 12, further comprising a follicular unit removal tool having a lumen therethrough, the removal tool is connected to and manipulated by the robotic arm to position the removal tool over a follicular unit located on a body surface; and wherein the control mechanism is adapted to align the lumen of the removal tool with a selected receptacle and urge the follicular unit through the removal tool into the selected receptacle.

16. The apparatus of claim 12, further comprising a presser foot operatively coupled with the control mechanism and configured to depress the body surface without penetrating it when the follicular unit is being expelled through the lumen of the implanting tool into the body surface.

17. An apparatus comprising:
a housing configured to accommodate two or more cartridges such that they are operatively connected to the apparatus, wherein each of the two or more cartridges comprises at least one indexing feature and a plurality of receptacles sized and configured to retain a biological unit;
an urging mechanism operative when substantially aligned with one of the plurality of receptacles to load the biological unit into the receptacle or expel the biological unit from the receptacle; and
an indexing mechanism comprising indexing features configured to simultaneously engage with an at least one indexing feature of a first cartridge and an at least one indexing feature of a second cartridge of the two or more cartridges when the first cartridge and the second cartridge are placed end-to-end and to simultaneously move the two or more cartridges in same direction to align a receptacle of the plurality of receptacles with the urging mechanism;
wherein the apparatus is configured such that the first and the second cartridge of the two or more cartridges are simultaneously operatively connected to the apparatus and wherein the urging mechanism is configured to move into alignment with a first receptacle of the second cartridge without disconnecting the first cartridge from the apparatus.

18. The apparatus of claim 17, the apparatus configured to automatically disconnect the first cartridge after at least one biological unit is expelled from or loaded into the first receptacle of the second cartridge.

19. The apparatus of claim 17, wherein the first cartridge comprises a first plurality of receptacles with a predetermined spacing therebetween and wherein the apparatus is configured to accommodate the first cartridge and the second cartridge in the housing such that a distance between a last receptacle of the first cartridge and a first receptacle of the second cartridge equals the predetermined spacing.

20. The apparatus of claim 17, further comprising an anti-popping feature configured to minimize potential expulsion of the biological units from a body surface.

* * * * *